United States Patent
Koosman et al.

(12)

(10) Patent No.: US 6,287,515 B1
(45) Date of Patent: Sep. 11, 2001

(54) CLEANING AND SANITIZING ASSEMBLY FOR CLEAN IN PLACE FOOD AND BEVERAGE AUTOMATIC DISPENSING MACHINES AND METHOD FOR USE THEREOF

(75) Inventors: Jerome M. Koosman, Hudson, WI (US); Brian R. Rudesill, Oakdale, MN (US)

(73) Assignee: Mesa Technologies, Inc., Hudson, WI (US)

( * ) Notice: Subject to any disclaimer, the term of this patent is extended or adjusted under 35 U.S.C. 154(b) by 0 days.

(21) Appl. No.: 09/304,914

(22) Filed: May 4, 1999

Related U.S. Application Data

(60) Provisional application No. 60/084,342, filed on May 5, 1999.

(51) Int. Cl.[7] ............................................. A61L 2/00
(52) U.S. Cl. ............................. 422/22; 422/22; 422/26; 422/28; 422/186.07
(58) Field of Search .................... 210/167, 292; 222/54, 190, 148; 422/292, 22, 26, 28; 134/102.1, 102.2, 166 R, 169 R; 62/342; 366/144; 426/565, 146.6; 99/454

(56) References Cited

U.S. PATENT DOCUMENTS

| | | | |
|---|---|---|---|
| 4,836,420 | * | 6/1989 | Kromrey ............................ 222/148 |
| 5,016,446 | * | 5/1991 | Fiedler ............................ 222/146.6 |
| 5,082,558 | * | 1/1992 | Burris ................................. 210/167 |
| 5,329,950 | * | 7/1994 | Barinas ............................. 134/102.1 |
| 5,636,763 | * | 6/1997 | Furness .................................. 222/54 |
| 5,690,151 | * | 11/1997 | Rutter et al. ......................... 222/148 |
| 5,706,720 | * | 1/1998 | Goch et al. ............................ 99/454 |
| 5,799,832 | * | 9/1998 | Mayo .................................. 222/148 |

* cited by examiner

Primary Examiner—Robert J. Warden, Sr.
Assistant Examiner—Imad Soubra
(74) Attorney, Agent, or Firm—Weiss & Moy, P.C.; Jeffrey Weiss; Harry M. Weiss

(57) ABSTRACT

A cleaning and sanitizing assembly for automatic food and beverage dispensing machines is provided. The dispensing machine may be manufactured or retrofitted with the assembly. The assembly may also be a stand-alone assembly. The assembly includes at least one water line and at least one sanitizer line to introduce at least one sanitizer to conditioned water from the at least one water line. The at least one sanitizer may be ozone generated by an ozone generator from air filtered and dried in an air filter/dryer and then added to the water in an air flow apparatus. Other sanitizers may be added to the ozonated water or the conditioned water without the ozone. The sanitized water is introduced into the dispensing machine typically through a reservoir which normally contains the produce mix. The sanitized water is dispersed into the reservoir through a rinse tube or a spray nozzle extending across the top of each reservoir. Both the rinse tube and spray nozzle may be moved away from the reservoir should access to the reservoir become necessary. A cover over the rinse tube and spray nozzle prevents splashing of the sanitized water. From the reservoir, the sanitized water proceeds throughout the dispensing machine to self-clean food and beverage contact surfaces.

2 Claims, 4 Drawing Sheets

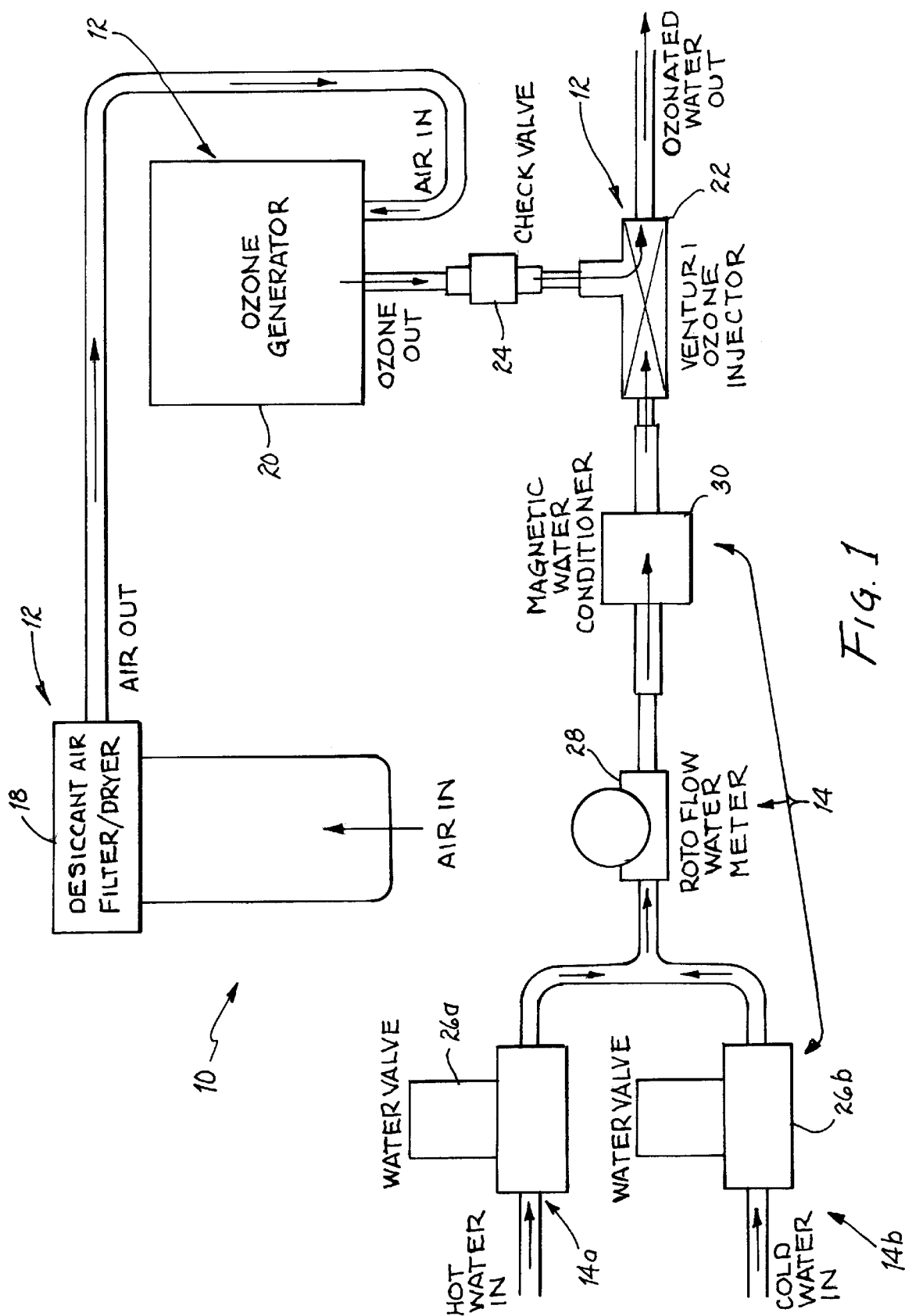

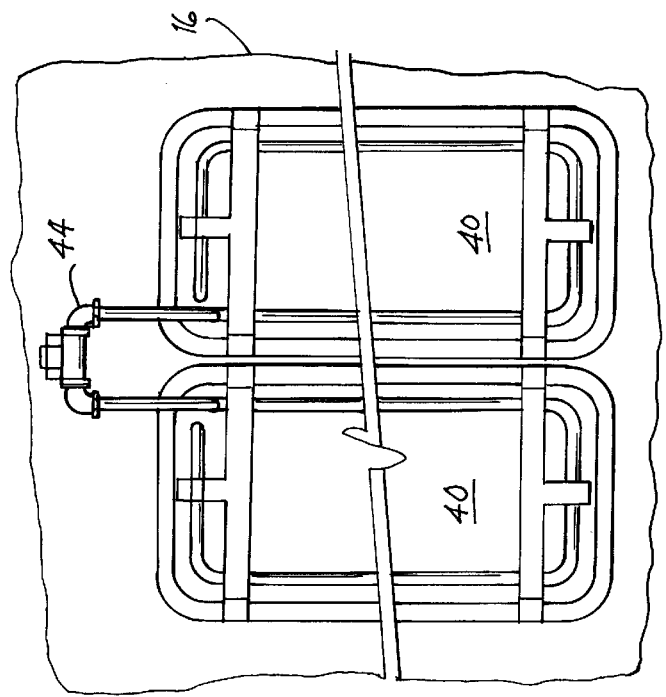
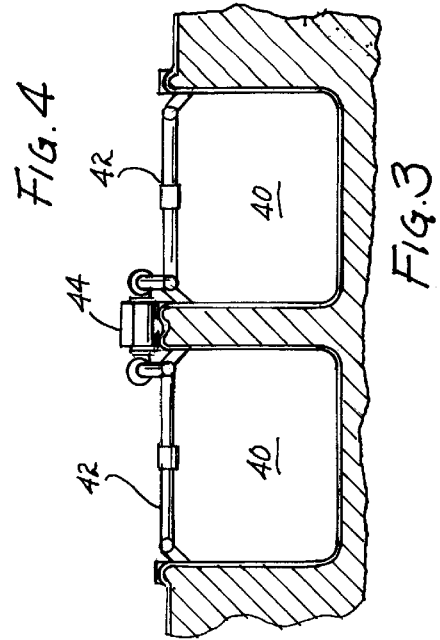
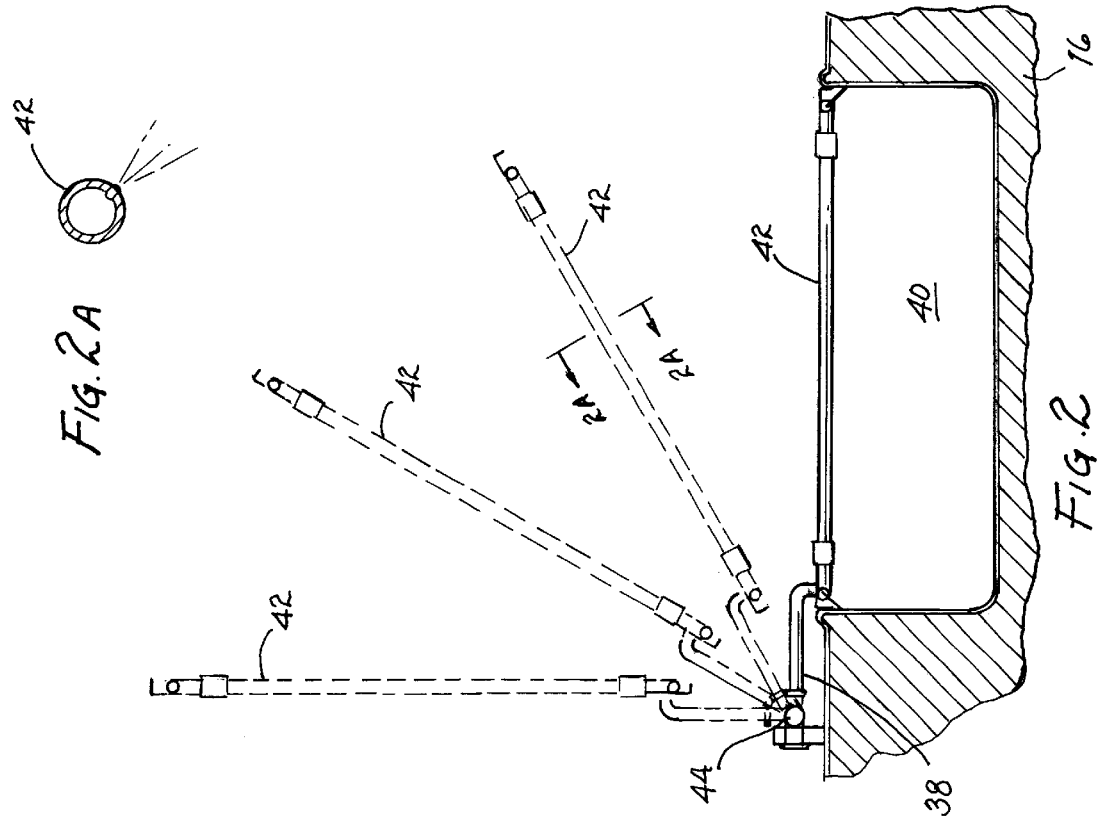

CLEANING AND SANITIZING ASSEMBLY FOR CLEAN IN PLACE FOOD AND BEVERAGE AUTOMATIC DISPENSING MACHINES AND METHOD FOR USE THEREOF

RELATED APPLICATION

This nonprovisional application claims priority from provisional application no. 60/084,342 filed on May 5, 1999.

FIELD OF THE INVENTION

This invention relates generally to a cleaning and sanitizing assembly for food and beverage machines and more specifically to an in-place cleaning and sanitizing assembly for food and beverage automatic dispensing machines.

BACKGROUND OF THE INVENTION

Ozone has been awarded GRAS (Generally Recognized as Safe) status by the FDA as a food preservative and disinfectant to increase product yield and shelf life. Ozone's utility as a chemical replacement to chlorine and its related compounds for disinfecting food contact surfaces has also been recognized. Ozone is a stronger oxidant than chlorine and acts faster over a wider spectrum of organisms than does chlorine and its related compounds. Moreover, there are proposed new regulations tightening limits on disinfection by-products (DBPs) on food surfaces and discharged process water. The use of ozone for disinfecting food contact surfaces presents less potential for generating undesirable residues and DBPs than does chlorine. Despite these recognized benefits, the use of ozone for disinfecting food contact surfaces has been limited.

Dispensing machines, including frozen dessert dispensing machines, are subject to bacterial contamination. Food and Drug Administration regulations require that frozen dessert dispensers in commercial use be cleaned at least once per day. To thoroughly clean these machines, it has been necessary to completely disassemble substantial portions of the machine prior to cleaning. This disassembly can be time consuming and labor intensive requiring extensive training. Moreover, some of the disassembled parts have been left soaking in disinfecting solution sometimes causing pitting or other damage to the part thus shortening its life. Disassembly also poses a risk to the operator because of contact with the cleaning chemicals. Importantly, the consequences of improper or incomplete cleaning by an operator can be hazardous. For example, if the operator "misses a spot", the cleaning solution is too weak, etc., there can be unchecked bacterial contamination. The cleanliness of the operator doing the cleaning is also significant.

Accordingly, there has been a need for a cleaning and sanitizing assembly and method that are simple to use and effective for cleaning and sanitizing automatic food and beverage dispensing machines. There is further a need for a cleaning and sanitizing assembly and method that permit the automatic dispensing machines to remain assembled during the cleaning process for cleaning and sanitizing in place. There is an additional need for a cleaning and sanitizing assembly and method that are fully automated to substantially prevent contamination caused by human error. There is a still further need for a cleaning and sanitizing assembly and method that may be added to an automatic dispensing machine as a stand-alone unit or as part of the manufactured or retrofitted automatic dispensing machine. The present invention fulfills these needs and provides other related advantages.

SUMMARY OF THE INVENTION

In accordance with this invention, it is an object of this invention to provide a cleaning and sanitizing assembly and method that are simple to use and effective for cleaning and sanitizing automatic food and beverage dispensing machines.

It is another object of this invention to provide a cleaning and sanitizing assembly and method that permit the automatic dispensing machines to remain assembled during the cleaning process for cleaning and sanitizing in place.

It is another object of this invention to provide a cleaning and sanitizing assembly and method that are fully automated to substantially prevent contamination caused by human error.

It is still another object of this invention to provide a cleaning and sanitizing assembly and method that may be added to an automatic dispensing machine as a stand-alone unit or as part of the manufactured or retrofitted automatic dispensing machine.

The cleaning and sanitizing assembly comprises, generally, at least one water line and at least one sanitizer line for introducing at least one sanitizer into the water from at least one water line to produce sanitized water for delivery to automatic food and beverage dispensing machines for in-place cleaning and sanitizing thereof. The assembly may also include means for dispersing the sanitized water into the automatic dispensing machine.

The at least one water line preferably includes both a hot and a cold water line from at least one water supply. Each of the hot and cold water lines flow through a valve, preferably an electronically-controlled solenoid valve, into a water metering device and then through a water conditioner before being added to the at least one sanitizer.

The at least one sanitizer line preferably is an ozone generation line. The ozone generation line includes an air filter/dryer, an ozone generator, and an air flow apparatus to introduce the ozone into the conditioned water.

The ozone generation line may be used alone or in combination with one or more other sanitizer lines that introduce a sanitizer other than ozone to the ozonated water through a pump before delivery to the automatic dispensing machine. Alternatively, such sanitizer lines may be used alone without the ozone generation line. Such other sanitizers include chlorine or other FDA-approved sanitizer.

The sanitized water, ozonated or otherwise, is delivered to the automatic dispensing machine and dispersed therein usually initially to at least one reservoir of the automatic dispensing machine and then to other areas of the machines. In a preferred embodiment, the sanitized water is dispersed into the reservoir through a rinse tube extending over the top of each of the at least one reservoir. Each rinse tube includes a plurality of slits for flowthrough of the sanitized water. The rinse tube is connected to the water supply line through a swivel union. The swivel union permits an operator to lift the rinse tube away from the reservoir should access to the reservoir become necessary.

Each of the at least one reservoir also includes an overlying cover placed over the at least one reservoir and rinse tube to substantially prevent splashing of the sanitized water. The cover may be fully removable or movably hinged to the top of each of the least one reservoir.

In an alternative embodiment, the sanitized water is dispersed into the reservoir through a spray nozzle extending downwardly into an upper portion of each of the at least one reservoir through an opening in the cover. The spray nozzle may be connected to the cover in a manner substantially blocking the opening so as to substantially prevent splashing of the sanitized water when using the spray nozzle. Along with the cover, the spray nozzle may also be moved away from the reservoir by the swivel union. In the alternative embodiment, the swivel union is connected to a spray nozzle inlet tube terminating at about a 90 degree angle in the spray nozzle.

Although dispersion into the at least one reservoir of the automatic dispensing machine has been described, it is to be understood that sanitized water from the cleaning and sanitizing assembly may be delivered to places other than the reservoirs of automatic food and beverage dispensing machines. For example only, sanitized water from the cleaning and sanitizing assembly may be delivered to hoses, etc. i.e. to any food and beverage contact surfaces.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a schematic view of an ozone cleaning and sanitizing assembly embodying the invention, illustrating the introduction of ozone from an ozone generation line into water from a water line to produce ozonated water for in-place cleaning and sanitizing automatic self-cleaning food and beverage dispensing machines;

FIG. 2 is a side sectional view of a reservoir that may be found in an automatic food and beverage dispensing machine, illustrating a rinse tube across the top of the reservoir in an operational position with the rinse tube shown in phantom lines at three different positions when lifted away from the reservoir by a swivel union;

FIG. 2A is a cross-sectional view of the rinse tube of FIG. 2;

FIG. 3 is a sectional front view of a pair of reservoirs illustrating a rinse tube in the operational position across the top of each reservoir, the swivel union connecting the rinse tubes;

FIG. 4 is a top view of the pair of reservoirs of FIG. 3;

DETAILED DESCRIPTION OF THE PREFERRED EMBODIMENTS

Figure 5:
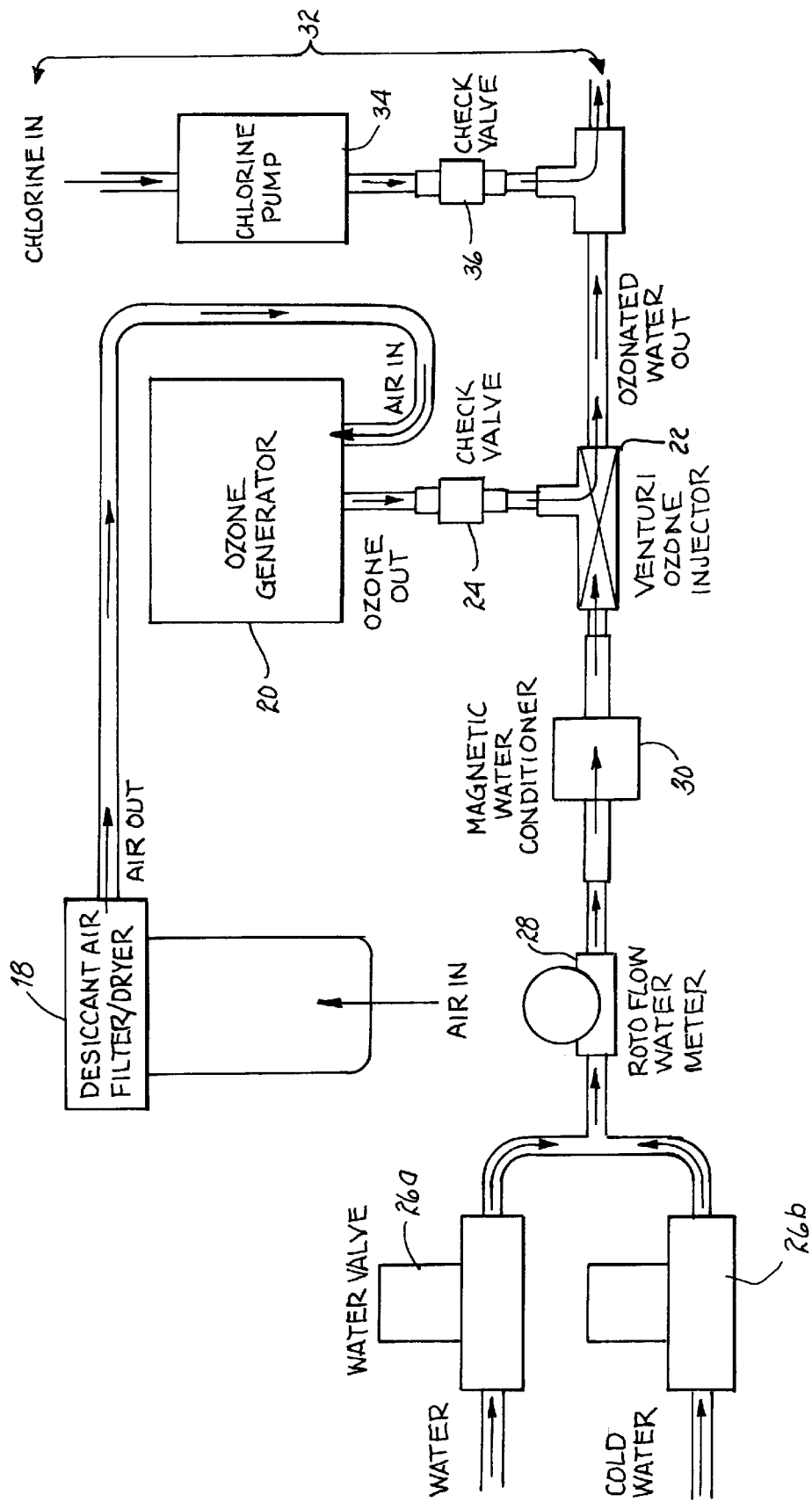
FIG. 5 is a schematic view of the assembly of FIG. 1 illustrating the ozone generation line shown in FIG. 1 and another exemplary sanitizer line for addition of chlorine through a pump to the ozonated water.

As shown in the drawings for purposes of illustration, the present invention is concerned with a cleaning and sanitizing assembly, generally designated in the accompanying drawings by the reference number 10. The cleaning and sanitizing assembly comprises, generally, at least one ozone generation line 12 and at least one water line 14. The assembly 10 may be stand alone or added to an automatic dispensing machine as originally manufactured or retrofitted therewith to make an automatic self-cleaning food and beverage dispensing machine.

In accordance with the present invention, and as illustrated with respect to a preferred embodiment in FIGS. 1–6, the assembly 10 is for use with dispensing machines 16 such as described and claimed in U.S. Pat. No. 5,799,832 to Mayo et al. Such automatic dispensing machines 16 use automatic valves (not shown) of various configurations. Exemplary automatic dispensing machines include, but are not limited to, food and beverage dispensing machines such as softserve, batch shake, coffee and soda dispensing machines, and livestock feed dispensing machines. The dispensing machines may be pressurized or gravity fed. In a pressurized machine, hoses are used to draw product mix from plastic bags or some other container starting from or located in a walk-in cooler or other holding device.

The at least one ozone generation line 12 is shown in FIG. 1. The ozone generation line 12 includes an air filter/dryer 18, an ozone generator 20 and an air flow apparatus 22 such as a venturi, pump, or other air-flow apparatus. The air filter/dryer 18 increases the volume of ozone generated by removing moisture from and filtering room air that is passed therethrough. The size of the filter/dryer 18 may vary depending on the application. The ozone generator 20 then manufactures ozone from the dehydrated and filtered room air by an electrical process. Such an ozone generator 20 is available from Aqua-Flo, Inc. of Baltimore, Md. From the ozone generator 20, the ozone flows through at least one check valve 24 before it enters the air-flow apparatus 22 for introduction into conditioned water produced by the at least one water line 14 as hereinafter described.

The at least one water line 14 may include hot and cold water lines 14a and 14b originating from a potable water source (not shown). The hot and cold water lines 14a and 14b each flow through respective water valves 26a and 26b, preferably electrically controlled solenoid valves. The amount of water flow may be controlled either by a flow meter 28 or through a computer program. The hot and cold water then preferably flows through a water conditioner 30 such as a magnetic oxidizing treatment apparatus or the like. The magnetic water conditioner breaks down the metals present in the water that may otherwise cling to surfaces and makes the water wetter by breaking down its binding ability. The conditioned water then flows through the venturi, pump, or other air-flow apparatus 22 to introduce ozone therein. The conditioned water mixes with the ozone via tiny air bubbles to produce ozonated water. Descaling or demineralizing chemicals may be added to the ozonated water. It must be noted that depending on water quality, it may not be necessary to condition the water in which case the water does not flow through a water conditioner.

The at least one water line 14 may also include a hot water line 14a alone, with the water heated to well-established bacteria destroying temperatures (e.g. 150 degrees Fahrenheit).

The ozone generation line 12 may be used alone or in combination with one or more other sanitizer lines 32 that introduce a sanitizer other than ozone to the ozonated water through a pump 34 and then another check valve 36 before delivery to the automatic dispensing machine 16 (See FIG. 5). Alternatively, such sanitizer lines may be used alone without the ozone generation line. Such other sanitizers include chlorine or other FDA-approved sanitizer. Water with ozone alone, ozone in combination with another sanitizer or the other sanitizer alone will hereinafter be referred to as "sanitized water."

The sanitized water is delivered into the dispensing machines, hoses or any other object to be sanitized through a sanitized water supply pipe 38. For example, the sanitized water may enter the dispensing machines 16 in at least one reservoir 40. The reservoirs 40 are normally used to hold, for example, product mix. The sanitized water flows through a rinse tube 42 connected to the sanitized water supply pipe 38. The rinse tube 42 is positioned over the top of the at least one reservoir (FIGS. 2 and 3) or, if a pressurized dispensing machine, into refrigerated hoses at their origins. The rinse tubes 42 are preferably made from stainless steel and have a plurality of slits (not shown) therein about one half inch apart through which the sanitized water is dispersed into the at least one reservoir 40. The slits (not shown) may be laser cut or made in some other manner. When not in use, the at least one rinse tube 42 may be swiveled out of the way by a swivel union 44 that connects adjacent rinse tubes. The water flows from the sanitized water supply line through the swivel unit into the rinse tube.

Figure 6:
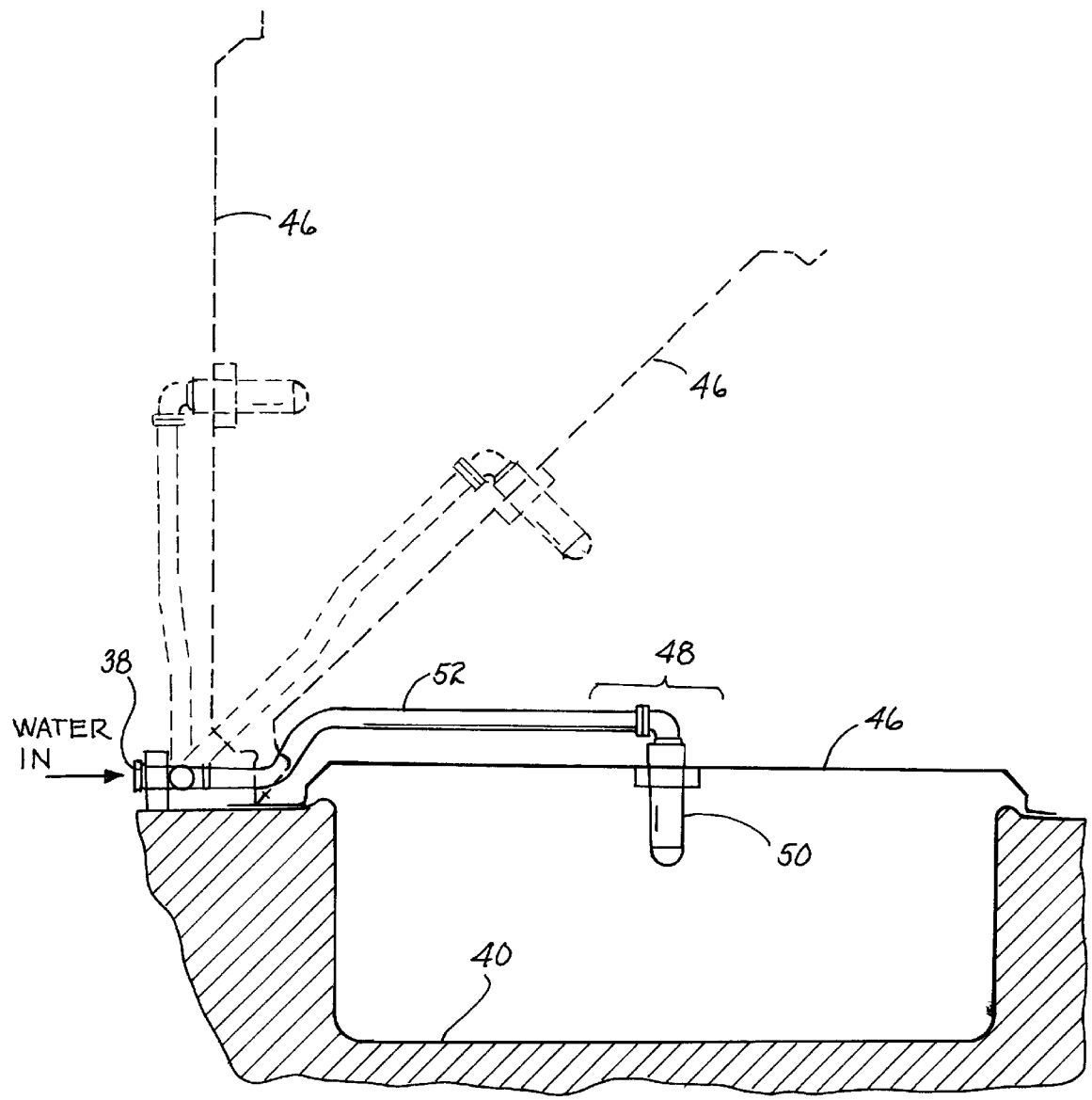
FIG. 6 is a sectional side view of an alternative embodiment illustrating a rotating spray nozzle connected by an spray nozzle inlet tube to the swivel union, the rotating spray nozzle blocking an opening in a hinged cover, the cover and rotating spray nozzle assembly shown in phantom when moved away from the top of the reservoir.

Each of the at least one reservoir 40 also includes a cover 46 that is either completely removable or movable in some manner to provide access to the reservoir. As shown in FIG. 6, the cover 46 may be hinged near a top surface of the reservoir 40. For example, if stubborn product residue is resistant to automatic cleaning as described herein, full or partial removal of the cover 46 away from the reservoir 40 is necessary to permit manual cleaning thereof. During automatic cleaning and sanitizing, the cover 46 is positioned across the top of the reservoir 40 over the rinse tube 42 to prevent splashing of the sanitized water outside the reservoir 40 which would otherwise cause harm to an operator of the machine. The cover 46 may preferably be made from Plexiglas, although over cover materials may be used. Additionally or alternatively, a switch (not shown) activated by movement of the cover 46 may be used to prevent operation of the self-cleaning cycle in the absence of the cover.

In an alternative embodiment, the sanitized water may be dispersed in the at least one reservoir 40 through a spray nozzle assembly 48. The spray nozzle assembly 48 includes a spray nozzle 50, preferably a rotating spray nozzle connected by an inlet tube 52 to the water supply pipe 38. A stationary spray nozzle may also be used. The inlet tube 52 terminates with the spray nozzle extending substantially downwardly therefrom at about a 90 degree angle. An exemplary rotating spray nozzle is available from Spraying System, Inc., Milwaukee, Wis. The swivel union permits the inlet tube 52 and connected spray nozzle 50 to be lifted out of the way as shown in FIG. 6.

In the alternative embodiment, the cover 46 may include an opening (not shown) for substantially downward passage of the spray nozzle into a top portion of the reservoir 40. The spray nozzle 50 is attached to the cover 46 in a manner substantially blocking the opening (not shown) to substantially block leakage of potentially hot sanitized water with or without chemicals. For example, the spray nozzle 50 may be bolted to the cover 46 around the circumference of the opening (not shown).

Although dispersion of the sanitized water into at least one reservoir is described, it must be noted that the sanitized water produced by the above assembly may be dispersed into or onto any food and beverage contact surface for cleaning and sanitizing thereof.

The efficacy of the ozonated water produced by the above-described assembly for cleaning and sanitizing a soft serve ice cream dispensing machine modified for automated sanitization such as described in U.S. Pat. No. 5,799,832 to Mayo et al. was tested using American National Standard/ NSF International Standard 6 (ANSI/NSF6) for Dispensing Freezers (Section 6.1-cleaning and santitization procedures). The dispensing soft serve freezer was filled with soft serve mix inoculated with a culture of E.coli to achieve a final concentration of approximately 1×10 colony forming units (cfu)/milliliter of E. coli in the soft serve mix. After allowing the inoculated soft serve to contact all surfaces, the soft serve was dispensed and tested until the unit reservoir was empty. The unit went through a programmed ozone washing, sanitizing and rinse cycle. After completion of this cycle, sterile phosphate buffered distilled water was added to the unit reservoirs and ten 50-milliliter samples of the buffer were collected at intervals from full reservoirs to empty reservoir. Samples were collected in sterile microbiological containers, transported to the laboratory and E.coli enumerated with Violet Red Bile (VRB) agar and Brilliant Green Bile (BGB) broth.

To run the ozonated water through the dispensing machine, a computer program was activated when the unit operator depressed a button controlling the self-cleaning process. Before cleaning, the reservoirs needed to be purged until the low level light came on. Thereafter, no operator action was required. Generally, ozonated hot water of at least 150 degrees Fahrenheit was dispensed into each of the reservoirs through their respective rinse tubes. The hot ozonated water sprayed down the side of each reservoir, melting any residual product and washing it into the freezing cylinders. The augers in the freezing cylinders were then activated to melt any residual product. This cycle was repeated with dirty water dispensed automatically from the spigots by opening and closing the valves on each cycle. A dispensing funnel connected to a hose was attached with the hose carrying runoff into a container or drain. After a few cycles, the residual product was removed. Ozonated cold water rinse cycles were then initiated. During the automated ozone rinse and sanitizing procedure, ozone concentrations in the rinse water coming from the test unit reservoirs were monitored on-site using a LaMotte ozone field analysis kit. The concentration of ozone in the sanitizing rinse water was detected by the kit at 0.6 mg/L. Ozone as not detected in the final rinse water from the test unit reservoirs. A residue test was also performed to determine if there was any ozone in the dispensing machine after sanitizing was complete. The tests showed no ozone residue present.

The test results showed the concentration of E.coli in the test units after cleaning and sanitizing to be reduced to non-detectable levels (less than 1 colony forming units per millimeter) from the initial inoculated mix E.coli concentrations of >200,000 colony forming units per millimeter.

From the foregoing, it is to be appreciated that the entire cleaning operation may be run by computer such as a computer connected to the dispensing machine or a chip embedded in the control board of the dispensing machine. The use of a modem to call the dispensing machine and adjust the settings for the cleaning process may also be used.

Although a particular embodiment of the invention has been described in detail for purposes of illustration, various modifications may be made without departing from the spirit and scope of the invention. Accordingly, the invention is not to be limited, except as by the appended claims.

We claim:

1. A method for cleaning a soft serve dispensing machine in place comprising the steps of:

providing a soft serve dispensing machine having at least one reservoir;

providing at least one water line including a metering device and a water conditioner;

providing an ozone generation line including an air filter/dryer, an ozone generator, and an air flow apparatus to introduce ozone into water from said at least one water line to produce ozonated water;

providing means for dispersing said ozonated water into said at least one reservoir in said soft serve dispensing machine;

purging said at least one reservoir;

dispensing said ozonated water at a temperature of approximately 150 degrees Fahrenheit into said at least one reservoir;

wherein said ozonated water has a concentration of ozone of about 0.6 mg/L; and dispensing said ozonated water after passing through said at least one reservoir from said soft serve dispensing machine.

2. The method of claim 1 further comprising the step of dispensing cold said ozonated water into said at least one reservoir after said step of dispensing said ozonated water at a temperature of approximately 150 degrees Fahrenheit into said at least one reservoir.

* * * * *